United States Patent [19]
Pawloski

[11] 4,183,957
[45] Jan. 15, 1980

[54] N'-(SUBSTITUTED PHENYL)-N-(2-(HALOPHENOXY)ETHYL)ALKYLANIMIDAMIDES

[75] Inventor: Chester E. Pawloski, Bay City, Mich.

[73] Assignee: The Dow Chemical Company, Midland, Mich.

[21] Appl. No.: 945,158

[22] Filed: Sep. 25, 1978

[51] Int. Cl.$^2$ ............... C07C 123/00; A61K 31/155
[52] U.S. Cl. ............................. 424/326; 260/564 R
[58] Field of Search ................... 260/564 R; 424/326

[56] References Cited

U.S. PATENT DOCUMENTS

| 3,855,249 | 12/1974 | Lafon | 260/564 R |
| 3,888,927 | 6/1975 | Hamahawa et al. | 260/564 R |

OTHER PUBLICATIONS

Chemical Abstracts, vol. 65, column 2182(e), (1966).

*Primary Examiner*—Gerald A. Schwartz

[57] ABSTRACT

Novel N'-(substituted phenyl)-N-(2-(halophenoxy)ethyl)alkylanimidamides are disclosed. Their method of use in the control and kill of bacteria and fungi, and compositions containing the novel compounds as the active ingredients therein are claimed.

6 Claims, No Drawings

N'-(SUBSTITUTED PHENYL)-N-(2-(HALOPHENOXY)ETHYL)ALKYLANIMIDAMIDES

SUMMARY OF THE INVENTION

The novel compounds of the present invention, hereinafter alternatively referred to as "active compounds", are N'-(substituted phenyl)-N-(2-(halophenoxy)-ethyl)alkylanimidamides which correspond to the formula

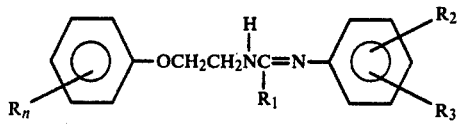

wherein R is Cl, Br or F; $R_1$ is $C_1$–$C_6$ alkyl and most preferably $C_1$–$C_3$ alkyl; $R_2$ and $R_3$ are independently selected from H, halogen, or $C_1$–$C_3$ alkyl; and n is 0, 1, 2 or 3.

The active compounds, directly or as active ingredients in formulations and compositions, exhibit, when used in antimicrobially-effective amounts, antimicrobial activity against fungi and bacteria. Hereinafter the terms "antimicrobial" and "antimicrobially-effective" when used in conjunction with the active compounds will be employed to identify their activity against fungi and/or bacteria.

The term halogen is used in the specification and claims to represent chlorine, fluorine and bromine.

The terms "$C_1$–$C_3$ alkyl" and "$C_1$–$C_6$ alkyl" are used herein and in the appended claims to designate straight or branched chain alkyl groups containing, respectively, 1 to 3 and 1 to 6 carbon atoms.

The active compounds are prepared by reacting $POCl_3$ and an appropriate N-(2-phenoxy)ethyl)amide of the formula

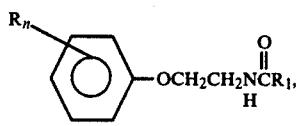

wherein R, $R_1$ and n are as set forth above, in 1,2-dichlorethane. The thus-formed mixture is stirred at about 50° C. to about 60° C., and preferably at about 55° C. to about 60° C., for about 1 to about 5 hours, and is thereafter allowed to cool to approximately 25° C., whereupon an appropriate aniline of the formula

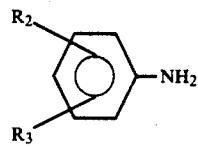

wherein $R_2$ and $R_3$ are as set forth above, is added to the mixture. The thus-formed reaction mixture is stirred at reflux until substantial completion of the reaction, usually from about 8 to about 16 hours. In order to obtain the desired product from its acid salt, it is generally necessary to make the product mixture slightly basic, such as by adding a 20% NaOH water solution. The product layer is separated, washed with water, dried, filtered and distilled. The resulting product is a thick oil which can be used as prepared, however, if desired, it can be further purified by conventional techniques known to one skilled in the art.

Ordinarily substantial equimolar proportions of the starting materials are employed. However, the aniline starting material may be used in slight excess of the stoichiometric requirements.

DESCRIPTION OF THE PREFERRED EMBODIMENTS

The following examples illustrate the present invention and the manner by which it can be practiced but as such should not be construed as limitations upon the overall scope of the same.

EXAMPLE 1

Preparation of N'-(4-Chloro-2-methylphenyl)-N-(2-(2,4-dichlorophenoxy)ethyl)propanimidamide (Compound 1)

A mixture of 19.5 g (0.075 mole) of N-(2-(2,4-dichlorophenoxy)ethyl)propylamide, 11.4 g (0.075 mole) $POCl_3$ and 250 mls of 1,2-dichloroethane was stirred at 60° C. for six hours. The mixture was cooled to 25° C., whereupon 10.4 g (0.075 mole) of 4-chloro-2-methylaniline was added thereto. An exotherm was noted. The mixture was refluxed for 10 hours and allowed to cool. The product mixture was made basic with a 20% NaOH water solution. The product layer was separated, washed once with 200 ml of water, dried over sodium sulfate, filtered and distilled under reduced pressure to give 65% yield (based on the amide) of the desired product, a thick oil, b.p. 142° C./1.3 mm Hg. NMR confirmed the assigned structure:

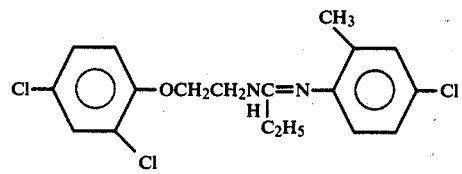

EXAMPLE 2

Preparation of N'-(4-chloro-2-methylphenyl)-N-(2-(2,4,5-trichlorophenoxy)ethyl)ethanimidamide (Compound 2)

Following the general procedure of Example 1, but using the appropriately substituted starting materials, Compound 2 was prepared in 50% yield (calculated from the amide). The desired product was a thick oil, b.p. 140° C./1.0 mm Hg. NMR confirmed the assigned structure:

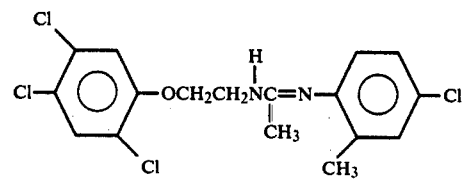

EXAMPLE 3

Preparation of N'-(4-chloro-2-methylphenyl)-N-(2-(2,4,5-trichlorophenoxy)ethyl)propanimidamide (Compound 3)

Following the general procedure of Example 1, but using the appropriately substituted starting materials, Compound 3 was prepared in 58% yield (calculated from the amide) as a thick oil, having a refractive index, at 25° C., of 1.5946. NMR confirmed the assigned structure:

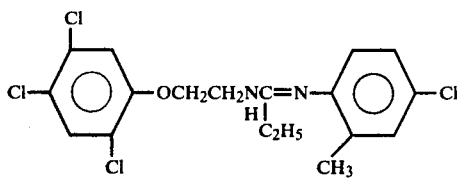

EXAMPLE 4

Preparation of N'-(4-chloro-2-methylphenyl)-N-(2-(2,4-dichlorophenoxy)ethyl)ethanimidamide (Compound 4)

A mixture of 20 g (0.086) mole of N-(2-(2,4-dichlorophenoxy)ethyl)acetamide, 12.4 g (0.086 mole) of POCl$_3$ was stirred at 50°-60° C. for five hours. After cooling to ~25° C., 12.2 g (0.086 mole) of 4-chloro-2-methylaniline was added to the mixture. An exotherm was noted. The reaction mixture was stirred at reflux for eight hours, allowed to cool, and then made basic with a 20% NaOH water solution. An emulsion was obtained making phasing difficult. The solution was made slightly acidic and phasing was obtained. The product layer was separated, dried over potassium carbonate, filtered and distilled under reduced pressure. The resulting oil was heated in 200 mls toluene, filtered hot and cooled. The toluene phase was poured into 200 mls of n-hexane and cooled to dry ice/acetone bath temperatures. The solids obtained were filtered off. The liquid phase was distilled under reduced pressure to produce 8.2 g (26% yield from the amide) of a thick oil, having a refractive index, at 25° C., of 1.6013. NMR spectra confirmed the assigned structure:

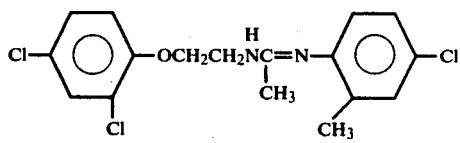

The N-(2-phenoxy)ethyl)amide starting material may be prepared by reacting an appropriate phenol with an appropriate oxazoline, both of which are available commercially, in accordance with the following equation;

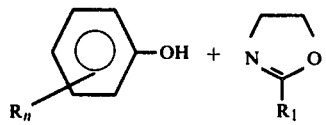

The oxazoline and phenol are mixed in equimolar proportions in a solvent such as ethyl benzene, and heated to ~120° C. until the reaction is substantially complete, usually from about 18 to about 24 hours. The resulting product mixture may be directly utilized in the preparation of the active compounds, or the N-(2-phenoxy)ethyl)amide product may be recovered by distilling off the solvent, after which the desired product may be recrystallized by conventional means.

The aniline and POCl$_3$ starting materials are available commercially.

The active compounds of the invention are suitable for use as antimicrobials for the control of bacteria and fungi. This is not to suggest that the active compounds and mixtures thereof with usual additives are equally effective against all such organisms at the same concentration. The active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good control and kill are realized with compositions wherein antimicrobially-effective amounts of from about 50 to about 500 parts by weight of one or more of the active compounds per million parts of such compositions are employed. As stated hereinbefore the active antimicrobially-effective amount to be employed against a given organism or in a certain composition can be determined by one skilled in the art.

Incorporation of the active compounds of this invention into materials which are subject to fungal attack inhibits the growth of the fungi and preserves the original value of the materials. The active compounds are sufficiently nonvolatile and water-insoluble so that they will persist on or in such materials for long periods of time. Examples of materials which are adversely affected by fungal growth are latex and alkyl paint films, wood and wooden products. The active compounds are sufficiently active against fungi that only small quantities are required to prevent mildew on paint films or wood rot. The active compounds are therefore useful for long-term protection against fungal growth in or on materials having a wood basis or a protective or decorative paint film or other coating or covering subject to fungal attack.

In a standard activity test, samples of Compounds 1, 2 and 3 were individually dispersed in warm melted nutrient agar which was poured into petri dishes and allowed to solidify, the active compounds being employed in an amount sufficient to provide from 5 to 500 parts by weight thereof per million parts (ppm) of the ultimate agar composition. The surface of the agar was inoculated with a variety of bacterial and fungal pest organisms, and the inoculated plates incubated under conditions conducive to bacterial and fungal growth. Similar check plates in which the agar did not contain the active compounds or other toxic compounds were similarly inoculated and incubated.

In these studies, Compounds 1, 2 and 3 gave 100% growth inhibition (kill) and control of the following organisms, as set forth in the Table, at the indicated concentrations in parts per million (ppm);

TABLE

ANTIMICROBIAL ACTIVITY

| Organism | Concentration in ppm | | |
|---|---|---|---|
| | Cmpd 1 | Cmpd 2 | Cmpd 3 |
| S. aureus | 5 | 50 | 50 |
| S. typhosa | 100 | 50 | 50 |
| A. niger | 10 | 5 | 50 |
| A. fumigatus | 50 | 5 | 50 |
| C. pelliculosa | 50 | 10 | 50 |
| C. albicans | 100 | 10 | 50 |
| B. subtilis | 5 | 10 | 50 |
| A. aerogenes | 500 | 50 | 50 |
| P. aeruginosa | 100 | 500 | 500 |
| P. sp. strain 10 | 500 | 100 | 500 |
| E. coli | 500 | 50 | 50 |
| S. marcesens | 500 | 50 | 50 |
| T. sp. med. col. VI | 50 | 10 | 50 |
| C. ips | 5 | 5 | 10 |
| Tri. sp. mad. P-42 | 10 | 10 | 50 |
| T. mentagrophytes | 50 | 5 | 10 |
| P. chrysogesum | 10 | 5 | 50 |
| P. pullulans | 10 | 5 | 10 |
| K. pneumoniae | 500 | 50 | 50 |

What is claimed is:

1. A compound of the formula

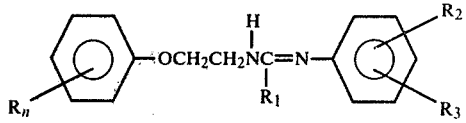

wherein R is Cl, Br or F; $R_1$ is $C_1$–$C_6$ alkyl; $R_2$ and $R_3$ are independently selected from H, halogen, or $C_1$–$C_3$ alkyl; and n is 0, 1, 2 or 3.

2. The compound of claim 1 which is N'-(4-chloro-2-methylphenyl-N-(2-(2,4-dichlorophenoxy)ethyl)ethanimidamide.

3. The compound of claim 1 which is N'-(4-chloro-2-methylphenyl)-N-(2-(2,4,5-trichlorophenoxy)ethyl)ethanimidamide.

4. The compound of claim 1 which is N'-(4-chloro-2-methylphenyl)-N-(2-(2,4-dichlorophenoxy)ethyl)-propanimidamide.

5. A method for controlling bacteria and fungi which comprises applying to said bacteria and fungi or their habitat an antimicrobially-effective amount of a compound of claim 1.

6. A composition for controlling bacteria and fungi comprising an antimicrobially-effective amount of a compound of claim 1 in combination with a solid or liquid diluent medium.

* * * * *